(12) United States Patent
Henderson et al.

(10) Patent No.: US 11,896,444 B2
(45) Date of Patent: *Feb. 13, 2024

(54) TISSUE MARKING DEVICE AND METHOD OF USE

(71) Applicant: DFC Medical LLC, Houston, TX (US)

(72) Inventors: Linda Henderson, Houston, TX (US); James Robert Henderson, Houston, TX (US)

(73) Assignee: DFC Medical LLC, Houston, TX (US)

(*) Notice: Subject to any disclaimer, the term of this patent is extended or adjusted under 35 U.S.C. 154(b) by 85 days.

This patent is subject to a terminal disclaimer.

(21) Appl. No.: 17/207,471

(22) Filed: Mar. 19, 2021

(65) Prior Publication Data

US 2021/0298870 A1    Sep. 30, 2021

Related U.S. Application Data

(63) Continuation of application No. 15/952,943, filed on Apr. 13, 2018, now Pat. No. 10,959,802.

(51) Int. Cl.
*A61B 90/00* (2016.01)

(52) U.S. Cl.
CPC ...... *A61B 90/39* (2016.02); *A61B 2090/3908* (2016.02); *A61B 2090/3983* (2016.02); *A61B 2090/3987* (2016.02); *A61B 2090/3991* (2016.02)

(58) Field of Classification Search
CPC .... A61B 2090/3908; A61B 2090/3966; A61B 2090/3987; A61B 2090/3991; A61B 5/064; A61B 5/4312; A61B 90/39
See application file for complete search history.

(56) References Cited

U.S. PATENT DOCUMENTS

| | | | |
|---|---|---|---|
| 5,556,410 A | 9/1996 | Mittermeir et al. | |
| 6,544,269 B2 | 4/2003 | Osborne et al. | |
| 6,905,484 B2 * | 6/2005 | Buckman | A61M 27/00 |
| | | | 604/174 |
| 8,437,834 B2 | 5/2013 | Carr, Jr. | |
| 8,718,745 B2 | 5/2014 | Burbank et al. | |
| 9,044,162 B2 | 6/2015 | Jones et al. | |
| 10,524,875 B2 | 1/2020 | Hermann et al. | |
| 10,959,802 B1 * | 3/2021 | Henderson | A61B 90/39 |
| 2004/0097981 A1 | 5/2004 | Selis | |
| 2005/0143674 A1 | 6/2005 | Burbank et al. | |
| 2009/0000629 A1 | 1/2009 | Hornscheidt et al. | |
| 2010/0030149 A1 | 2/2010 | Carr, Jr. | |
| 2010/0204570 A1 | 8/2010 | Lubock | |
| 2011/0152611 A1 | 6/2011 | Ducharme et al. | |
| 2011/0319932 A1 | 12/2011 | Avelar et al. | |
| 2014/0309522 A1 | 10/2014 | Fullerton et al. | |
| 2017/0296294 A1 | 10/2017 | Hermann et al. | |
| 2018/0035914 A1 | 2/2018 | Fullerton et al. | |
| 2020/0121414 A1 | 4/2020 | Springs et al. | |

FOREIGN PATENT DOCUMENTS

| | | |
|---|---|---|
| WO | 2020/068658 A1 | 4/2020 |
| WO | 2021/217007 A1 | 10/2021 |

* cited by examiner

*Primary Examiner* — Christine H Matthews
(74) *Attorney, Agent, or Firm* — BakerHostetler

(57) ABSTRACT

A tissue marking device enables the deployment of a hook to mark a location within a breast. The deployment is performed by inserting a needle in tissue until it arrives at a target location and pressing on the end of a rod that embeds the hook in the tissue. A thread is attached to the hook and is left exposed to facilitate locating the hook.

19 Claims, 5 Drawing Sheets

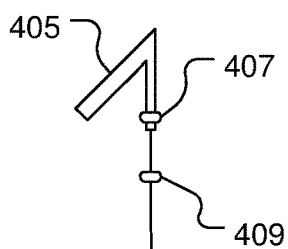
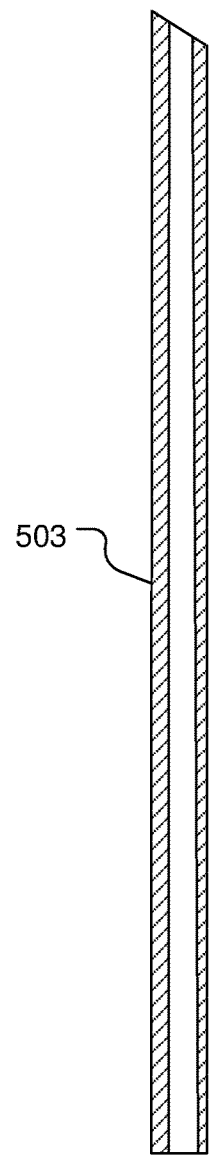
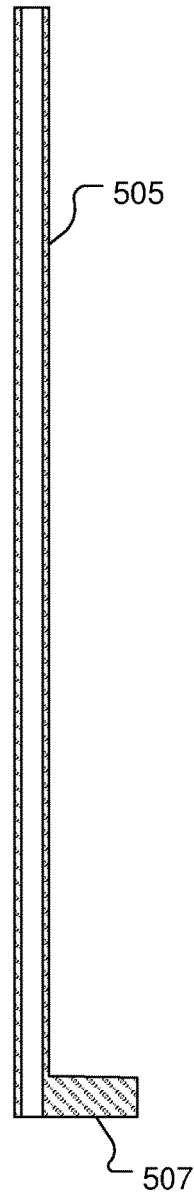
FIG. 4
FIG. 5

TISSUE MARKING DEVICE AND METHOD OF USE

CROSS-REFERENCE TO RELATED APPLICATIONS

This application is a continuation of U.S. patent application Ser. No. 15/952,943 filed Apr. 13, 2018, the entire contents of which are incorporated by reference herein.

1. FIELD OF THE INVENTION

The present invention relates generally to surgical tissue identification and removal, and more specifically, to a marking specific tissues within a breast for removal prior to surgery.

2. DESCRIPTION OF RELATED ART

Tissue marking is well known in the art and are effective means to indicate which tissue is to be tracked or removed. For example, FIGS. 1A and 1B depict a conventional wire marker device 101 having semi-rigid wire 103 with a hook 105 at the far end 107. During use, the wire 103 is forced through a needle 109 that is positioned near target tissue 111 of a breast 113 until the hook 105 emerges, releasing the hook 105 in the tissue 111. The needle 109 is removed leaving the wire protruding from the skin 115. The wire 103 and hook 105 enable a surgeon to quickly locate and remove the marked tissue 111.

One of the problems commonly associated with device 101 is its limited use. For example, the process of locating and marking the tissue requires the use of ultrasound and x-ray machines and is lengthy. The wire 103 is rigid and if pushed the hook 105 could be displaced limiting the time of marking to just prior to surgery to avoid displacing the hook 105.

Additionally, the patient is generally at unease prior to a surgery and it would be beneficial to perform the marking on a different day to relieve the pressure of the pending surgery. The time required to mark the tissue can be extensive further straining the patient.

Accordingly, although great strides have been made in the area of tissue marking, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 4 is a side view an alternative embodiment of the hook and thread of FIGS. 2A and 2B;

FIG. 5 is a cross-sectional side view of an alternative embodiment of the needle of FIGS. 2A and 2B.

DETAILED DESCRIPTION OF THE PREFERRED EMBODIMENT

Figure 1A:
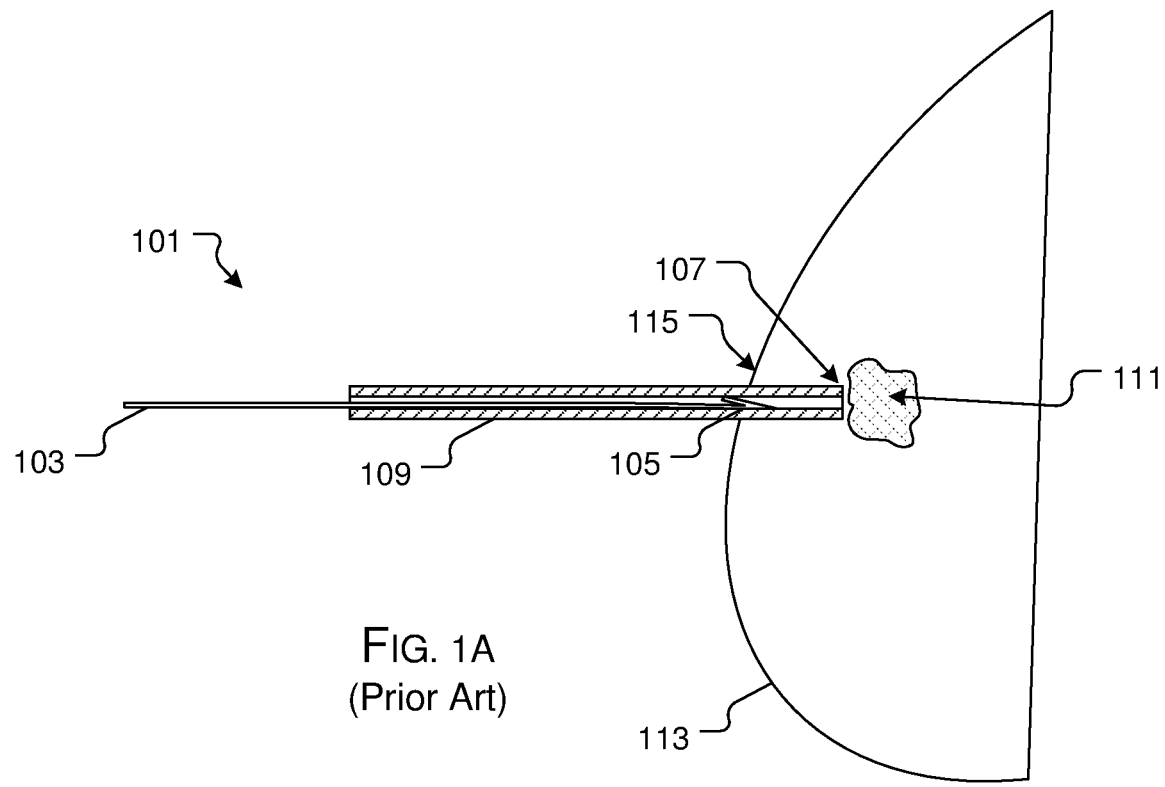
FIGS. 1A and 1B are cross-sectional side views of a of a common wire marker device.
Figure 1B:
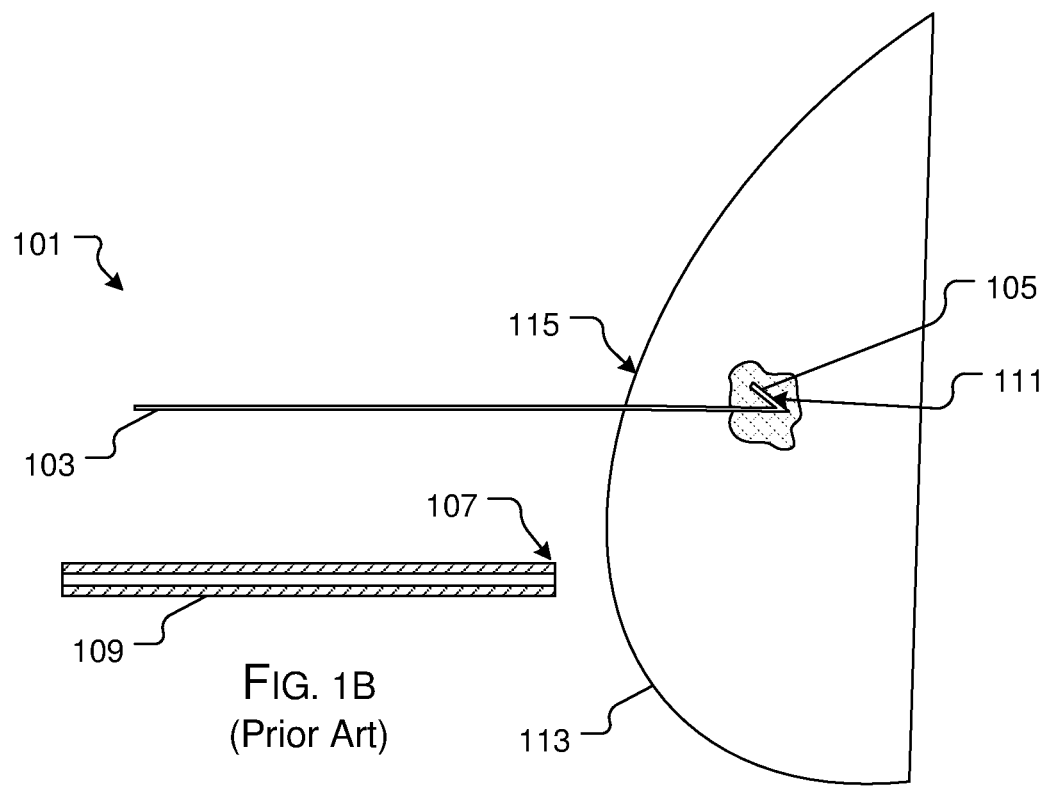

Illustrative embodiments of the device and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The device and method of use in accordance with the present application overcomes one or more of the above-discussed problems commonly associated with conventional wire marker devices. Specifically, the device of the present application enables the rapid marking of tissue days prior to the surgery. In addition, the device of the present application enables the patient to move about without discomfort or dislocating the hook marking the target tissue. These and other unique features of the device and method of use are discussed below and illustrated in the accompanying drawings.

The device and method of use will be understood, both as to its structure and operation, from the accompanying drawings, taken in conjunction with the accompanying description. Several embodiments of the device are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2A:
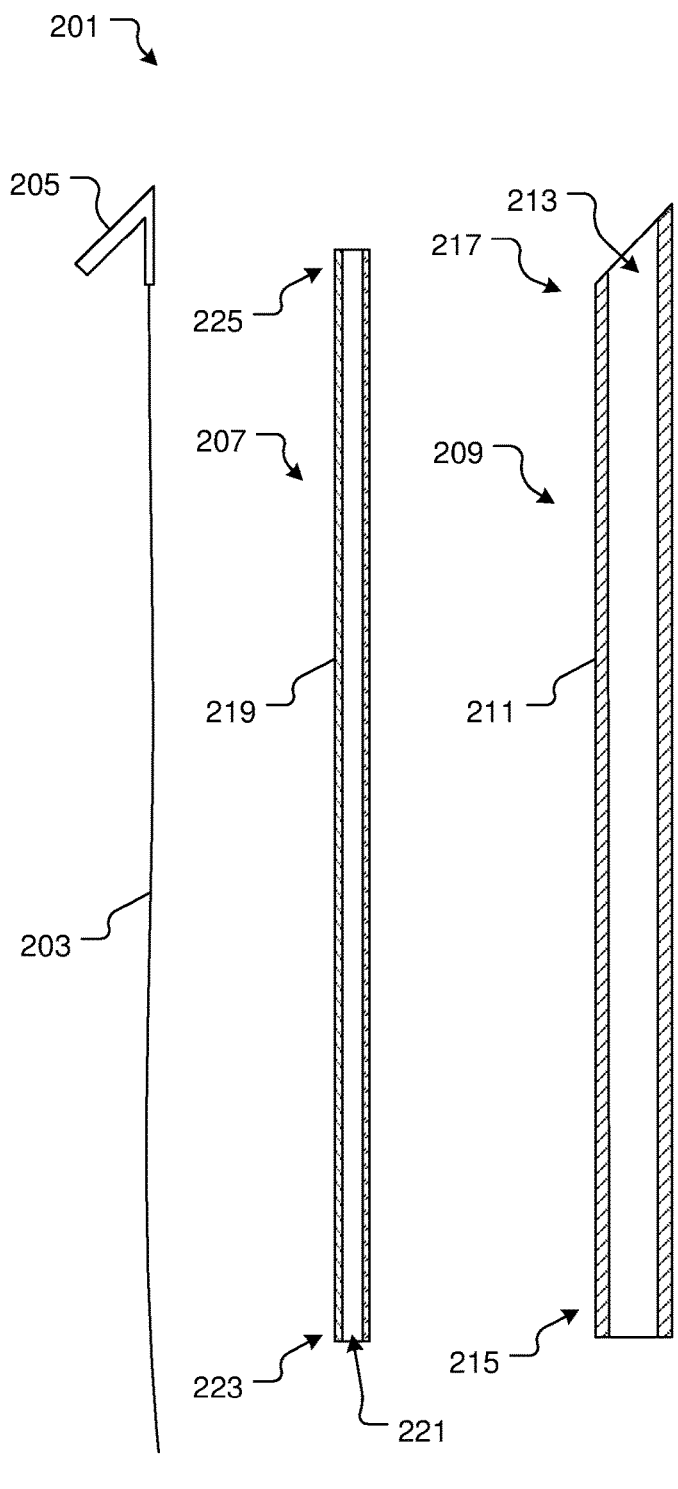
FIGS. 2A and 2B are cross-sectional side views of a tissue marking device in accordance with a preferred embodiment of the present application.
Figure 2B:
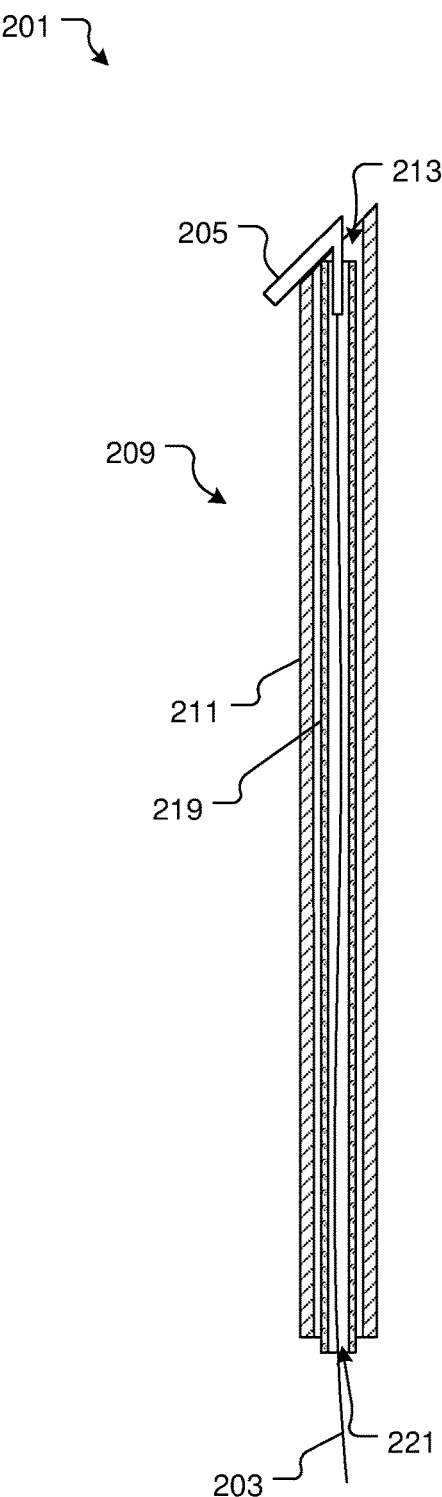

Referring now to the drawings wherein like reference characters identify corresponding or similar elements throughout the several views, FIG. 2 depicts a side view of a tissue marking device in accordance with a preferred embodiment of the present application. It will be appreciated that device 201 overcomes one or more of the above listed problems commonly associated with conventional wire marker devices.

In the contemplated embodiment, device 201 includes a thread 203 rigidly attached to a hook 205 that is embedded in targeted tissue 111 of a breast 113.

The hook 205 and thread 203 are deployed by a tool 207 once near tissue 111. The tool 207 including a needle 209 and a rod 219 configured to enter the breast 113 and place the hook 205 in the targeted tissue 111.

The needle 209 having a body 211 that encloses a first tube 213 open on a first end 215 and a second end 217. The rod 219 enclosing a second tube 221 also open on a first 223 end and second end 225. The rod configured to sit in the first tube 213 of needle 209 and hold hook 205 and thread 203. The thread 203 of a length so that it extends out of the second ends 217 and 225 of the needle 209 and rod 219 respectively.

Figure 3A:
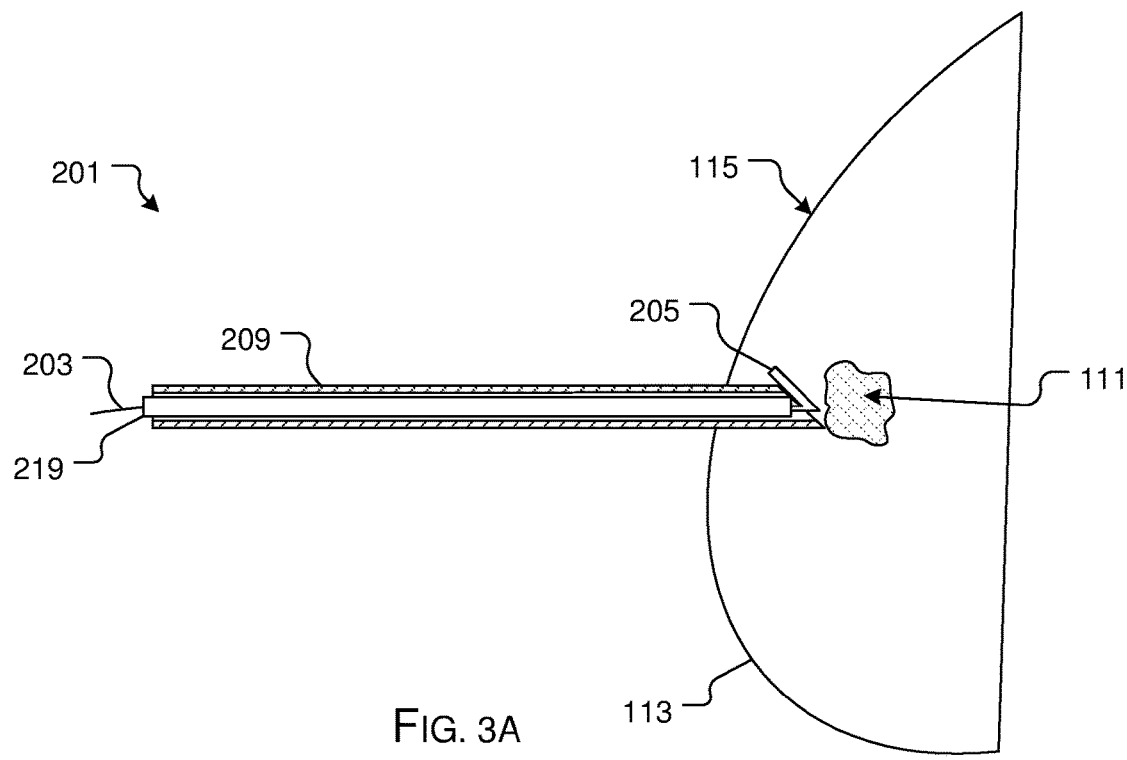
FIGS. 3A and 3B are cross-sectional side views of the device of FIGS. 2A and 2B in use.
Figure 3B:
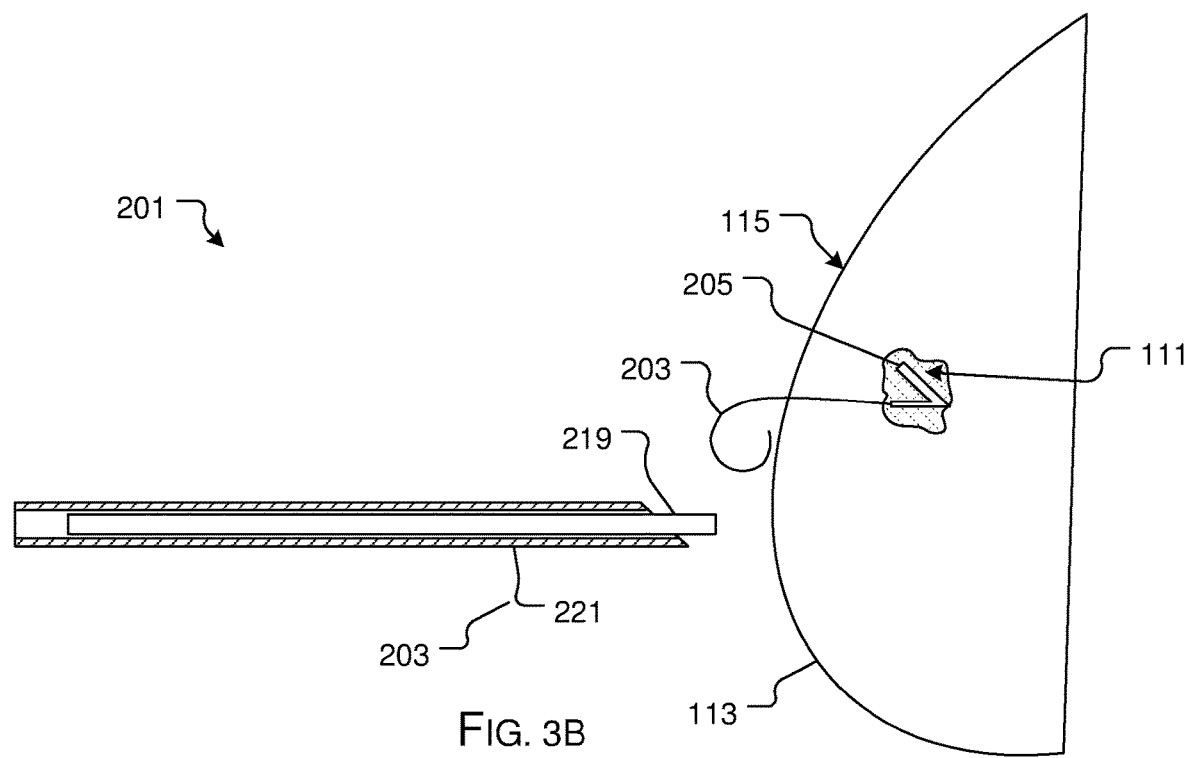

In use, the hook 205 is seated in the second end 225 of the rod 219 as depicted in FIGS. 3A and 3B. The tool 207 is forced in the breast 113 until the second end 217 of the needle 209 reaches the target tissue 111. The first end 223 of the rod 219 is pressed causing the hook 205 to extend past the second end 217 of the needle and embed in the tissue 111. The needle 209 and rod 219 are removed leaving the thread 203 protruding from the skin 115 and attached to the hook 205.

It should be appreciated that one of the unique features believed characteristic of the present application is that hook 205 can be embedded in a targeted tissue 111 and still enable a patient to perform most normal activities allowing the hook 205 to be placed far in advance of the surgery.

Referring now to FIG. 4 a side view of an alternative embodiment of the hook 205 and thread 203 is depicted. Embodiment 401 having a thread 403 rigidly attached to a hook 405. The hook 405 having a first marking band 407 rigidly attached. The thread 403 having a second marking band 409 rigidly attached. It will be appreciated that bands 407, 409 are configured to communicate a set distance to further facilitate the measurement of targeted tissue 111 or to distinguish between multiple marked tissues 111. It will be appreciated that any arrangement of marking 407, 409 bands is contemplated.

Referring now to FIG. 5 a cross-sectional side view of an alternative embodiment of the needle 209 and tool 207 are depicted. Embodiment 501 including a needle 503 and tool 505 the tool 505 having an elbow portion 507. The elbow portion 507 is configured to control the deployment of the hook 203. It will be appreciated that tool 505 is pushed until elbow portion 507 of the tool 505 contacts the needle 503. It will also be appreciated that elbow portion 507 is intended to limit the movement of tool 505 in needle 503 and that this same effect could be achieved with other stopping methods such as rubber or plastic stoppers could be used.

Figure 6:
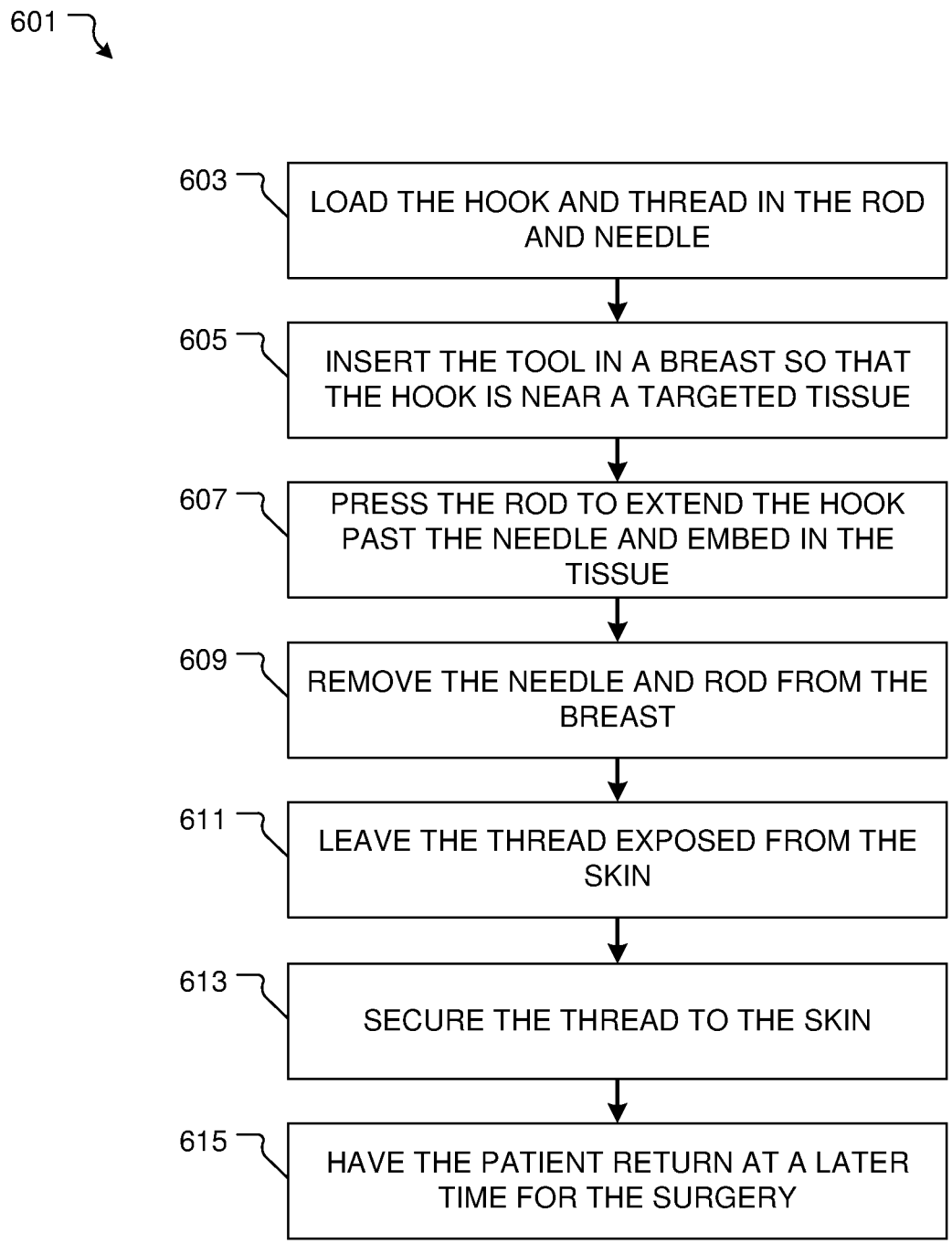
FIG. 6 is a flowchart of the preferred method of use of the device of FIGS. 2A and 2B. While the device and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

Referring now to FIG. 6 the preferred method of use of device 201 is depicted. Method 601 including loading the hook and thread in the rod and needle 603, inserting the tool in a breast so that the hook is near a targeted tissue 605, pressing the rod to extend the hook past the needle and embed in the tissue 607, removing the needle and rod from the breast 609, leaving the thread exposed from the skin 611, securing the thread to the skin 613 and having the patient return at a later time for the surgery 615.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed:

1. A tissue marking device for marking a targeted tissue in a breast of a patient, the device comprising:
   a thread of flexible construction rigidly attached to a hook, the thread having at least one marking band rigidly attached thereto and elevated from a central axis thereof and the hook having at least one marking band rigidly attached thereto and elevated from a central axis thereof; and
   a tool for positioning the hook in the targeted tissue of a breast, the tool comprising:
      a needle comprising a body defining a first tube, the first tube having an open first end and an open second end;
      a rod comprising a second tube having an open first end and an open second end,
      wherein the rod is configured to pass through the first tube of the needle while the thread extends through the second tube of the rod out the open first end of the rod and the open first end of the needle,
      wherein the rod is configured to extend the hook into a patient's skin into the targeted tissue, and
      wherein the needle and the rod are each configured to be removed from the patient's skin leaving the thread protruding from the patient's skin.

2. The device of claim 1, wherein the tool rod comprises: an elbow portion at a first end, wherein the elbow portion is configured to stop movement of the rod in the needle.

3. The device of claim 1, wherein the rod comprises a rubber stopper at a first end, wherein the rubber stopper is configured to stop movement of the rod in the needle.

4. The device of claim 1, wherein the rod comprises a plastic stopper at a first end, wherein the plastic stopper is configured to stop movement of the rod in the needle.

5. The device of claim 1, wherein the at least one marking band rigidly attached to the hook is configured to visually communicate a set distance to facilitate measurement of the targeted tissue.

6. The device of claim 5, wherein the at least one marking band rigidly attached to the hook is further configured to tactilely communicate a set distance to facilitate measurement of the targeted tissue.

7. The device of claim 1, wherein the at least one marking band rigidly attached to the thread is configured to visually communicate a set distance to facilitate measurement of the targeted tissue.

8. The device of claim 7, wherein the at least one marking band rigidly attached to the thread is further configured to tactilely communicate a set distance to facilitate measurement of the targeted tissue.

9. A method of marking a targeted tissue in a breast of a patient, the method comprising:
   inserting the device of claim 1 in the breast of the patient such that the hook is near the targeted tissue;
   pressing the rod to extend the hook past the needle and embed the needle in the targeted tissue; and
   removing the needle and the rod from the breast.

10. The method of claim 9, further comprising:
    leaving the thread exposed from the patient's skin.

11. The method of claim 10, further comprising:
    securing the thread to the patient's skin.

12. The method of claim 11, wherein the inserting, pressing, and removing steps are performed at a first time, the method further comprising:

having the patient return at a second time, after the first time, for a surgery.

13. The method of claim 10, wherein the rod comprises an elbow portion at a first end, wherein the elbow portion is configured to stop movement of the rod in the needle.

14. The method of claim 10, wherein the rod comprises a rubber stopper at a first end, wherein the rubber stopper is configured to stop movement of the rod in the needle.

15. The method of claim 10, wherein the rod comprises a plastic stopper at a first end, wherein the plastic stopper is configured to stop movement of the rod in the needle.

16. The method of claim 9, wherein the at least one marking band rigidly attached to the hook is configured to visually communicate a set distance to facilitate measurement of the targeted tissue.

17. The method of claim 16, wherein the at least one marking band rigidly attached to the hook is further configured to tactilely communicate a set distance to facilitate measurement of the targeted tissue.

18. The method of claim 9, wherein the at least one marking band rigidly attached to the thread is configured to visually communicate a set distance to facilitate measurement of the targeted tissue.

19. The method of claim 18, wherein the at least one marking band rigidly attached to the thread is further configured to tactilely communicate a set distance to facilitate measurement of the targeted tissue.

\* \* \* \* \*